United States Patent
Papot et al.

(10) Patent No.: US 10,293,021 B2
(45) Date of Patent: May 21, 2019

(54) CONJUGATES AND PRODRUGS FOR TREATING CANCER AND INFLAMMATORY DISEASES

(71) Applicants: CENTRE NATIONAL DE LA RECHERCHE SCIENTIFIQUE, Paris (FR); UNIVERSITE DE POITIERS, Poitiers (FR)

(72) Inventors: Sebastien Papot, Poitiers (FR); Isabelle Opalinski, Mignaloux Beauvoir (FR); Brigitte Renoux, Nouaille Maupertuis (FR); Thibaut Legigan, Poitiers (FR)

(73) Assignees: CENTRE NATIONAL DE LA RECHERCHE SCIENTIFIQUE, Paris (FR); UNIVERSITE DE POITIERS, Poitiers (FR)

( * ) Notice: Subject to any disclaimer, the term of this patent is extended or adjusted under 35 U.S.C. 154(b) by 62 days.

(21) Appl. No.: 15/117,069

(22) PCT Filed: Feb. 6, 2015

(86) PCT No.: PCT/IB2015/050914
§ 371 (c)(1),
(2) Date: Aug. 5, 2016

(87) PCT Pub. No.: WO2015/118497
PCT Pub. Date: Aug. 13, 2015

(65) Prior Publication Data
US 2017/0095525 A1    Apr. 6, 2017

(30) Foreign Application Priority Data
Feb. 7, 2014    (FR) .................... 14 50956

(51) Int. Cl.
| A61K 38/00 | (2006.01) |
| A61K 38/07 | (2006.01) |
| A61K 47/60 | (2017.01) |
| A61K 47/54 | (2017.01) |
| A61K 47/64 | (2017.01) |

(52) U.S. Cl.
CPC ............ *A61K 38/07* (2013.01); *A61K 47/549* (2017.08); *A61K 47/60* (2017.08); *A61K 47/643* (2017.08)

(58) Field of Classification Search
None
See application file for complete search history.

(56) References Cited

U.S. PATENT DOCUMENTS 7,829,531 B2    11/2010  Senter et al.
2013/0144045 A1  6/2013  Papot et al.

FOREIGN PATENT DOCUMENTS

| WO | 2007011968 A2 | 1/2007 |
| WO | 2011145068 A1 | 11/2011 |

OTHER PUBLICATIONS

Felix Kratz et al. "Probing the Cysteine-34 Position Endogenous Serum Albumin with Thiol-Binding Doxorubicin Derivatives. Improved Efficacy of an Acid-Sensitive Doxorubicin Derivative with Specific Albumin-Binding Properties Compared to That of the Parent Compound", J. Med. Chem., vol. 45, No. 25, pp. 5523-5533, (2002).
International Search Report for PCT/IB2015/050914 dated Apr. 28, 2015 (4 pages).
Isabelle Tranoy-Opalinski et al. "Beta-Glucuronidase-responsive prodrugs for selective cancer chemotherapy: An update", European Journal of Medicinal Chemistry, Mar. 2014, vol. 74, pp. 302-313.
Thibaut Legigan et al. "Synthesis and biological evaluations of monomethylauristatin E glucuronide prodrug for selective cancer chemotherapy", European Journal of Medicinal Chemistry, Sep. 2013, vol. 67, pp. 75-80.
Kai Temming et al. "Evaluation of RGD-Targeted Albumin Carriers for Specific Delivery of Auristatin E to Tumor Blood Vessels", Bioconjugate Chemistry, vol. 17, No. 6, pp. 1385-1394, Nov. 1, 2006.
Thibaut Legigan et al. "Synthesis and Antitumor Efficacy of Beta-Glucuronidase-Responsive Albumin-Binding Prodrug of Doxorubicin", Journal of Medicinal Chemistry, vol. 55, No. 9, pp. 4516-4520, May 10, 2012.
Thibaut Legigan et al. "The First Generation of Beta-Galactosidase-Responsive Prodrugs Designed for the Selective Treatment of Solid Tumors in Prodrug Monotherapy", Angewandte Chemie, Nov. 12, 2012, vol. 51, No. 46, pp. 11606-11610.
Felix Kratz "Albumin as a drug carrier: Design of prodrugs, drug conjugates and nanoparticles", Jounal of Controlled Release, vol. 132, No. 3, Dec. 18, 2008, pp. 171-183.

*Primary Examiner* — Jeanette M Lieb
(74) *Attorney, Agent, or Firm* — Shumaker, Loop & Kendrick, LLP

(57) ABSTRACT

The present invention relates to the field of cancer and inflammatory diseases. More particularly, it aims to provide, for these purposes, novel conjugated forms of active ingredients belonging to the dolastatin family and having the formula as follows:

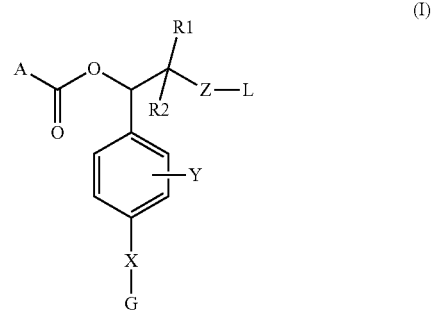

It is also directed towards prodrug forms of these conjugates.

17 Claims, 4 Drawing Sheets

CONJUGATES AND PRODRUGS FOR TREATING CANCER AND INFLAMMATORY DISEASES

FIELD OF THE INVENTION

The present invention relates to the field of cancer and inflammatory diseases. More particularly, the present invention aims to propose novel conjugated forms of active ingredients belonging to the dolastatin family.

TECHNOLOGICAL BACKGROUND

Cancer and inflammatory diseases are among the most common pathological ailments at the current time. In particular, cancer is today one of the primary causes of mortality in France and in most industrialized countries. Among the various treatment modes that can be envisaged, chemotherapy is the only one that can be used against circulating tumors, such as lymphomas and leukemias, and metastases.

Among the active agents that can be envisaged in chemotherapy are certain natural peptides like, in particular, dolastatin 10, a linear natural compound derived from the marine world, made up of four amino acids, three of which are specific thereto. Synthetic derivatives of dolastatin 10 are today also available and preferred. They are more particularly auristatin PE, auristatin E or monomethyl auristatin E (MMAE). Dolastatin, auristatin E and derivatives thereof have the property of inhibiting tubulin polymerization and of consequently preventing cell division (antimitotics).

However, these active agents of the dolastatin family are unfortunately, like other anticancer active agents clinically used, devoid of satisfactory selectivity with respect to tumor cells. Indeed, they also target healthy tissues. This non-selective destruction leads to severe side effects and results, in most cases, in premature arrest of the treatment.

The development of novel anticancer agents capable of selectively destroying tumors without affecting the healthy organs therefore represents a major interest in combating cancer.

One of the approaches retained for overcoming this lack of selectivity is based on the development of conjugates of these active agents. These conjugates, also called prodrugs, are thus usually obtained by grafting the active agent under consideration with an entity, the functions of which are to inactivate said active agent when it is in this prodrug form, to transport it to the target tissues or cells, and to promote its release at said target tissues or cells and then re-establish its curative biological activity. This approach is based more particularly on the observation of specificities peculiar to tumor tissues. Thus, it is known that the tumor microenvironment differs from healthy tissues by virtue of a more acid pH, a greater reducing potential, an increased permeability for macromolecules or else by virtue of the presence of a relatively high concentration of certain enzymes, such as, for example, β-glucuronidase. Likewise, it has been shown that diseased tissues differ from healthy tissues in that malignant cells over express at their surface membrane receptors or antigens which differentiate them from healthy cells, such as folic acid receptors or the CD33 antigen.

Consequently, derivatives of conventional active agents have already been developed in order to take advantage of these differences for the purpose of increasing, in particular, their selectivity for tumor cells.

Thus, monomethyl auristatin E (MMAE) has been conjugated to an anti-CD30 antibody by means of a cleavable arm (U.S. Pat. No. 7,829,531). However, such a conjugate has too great a specificity with respect to its target and proves to be barely effective or even ineffective with regard to cancers and/or inflammatory diseases which are non-CD30-dependent.

Teming et al. (2006, Bioconjugate Chem) have conjugated a monomethyl auristatin E (MMAE) molecule to an albumin unit, via a cleavable link, in order to target tumor tissues.

More recently, Legigan et al. (2013, Eur. J. Med. Chem.) and Tranoy-Opalinski et al. (2014, Eur. J. Med. Chem.) have conjugated a monomethyl auristatin E (MMAE) molecule to a glucuronyl unit via a self-reactive arm. This conjugated form of MMAE, also called prodrug, is inactive and only cleavage at the level of the tumor by β-glucuronidases, which are predominantly extracellular, enables the MMAE to perform its antimitotic biological activity. Nevertheless, rapid elimination of this prodrug by the kidneys is observed. Since the half-life of this prodrug is significantly reduced, it follows that it is necessary to increase the dosage, which is accompanied by harmful side effects.

Legigan et al. (2012, Angew. Chem. Int. Ed.) have also proposed a monomethyl auristatin E (MMAE) bi-functionalized with a galacto side group and a group which binds to folic acid receptors, the two groups being carried by a self-reactive arm. However, this prodrug requires a cell internalization step before being cleaved by an intracellular β-galactosidase and releasing the monomethyl auristatin E (MMAE).

Consequently, although these prodrug forms of monomethyl auristatin E are specifically transported to the tumor, their cytotoxic efficacy remains relative, and does not make it possible to envisage effective clinical treatment of a tumor.

There remains therefore a need for prodrugs of the dolastatin family which are capable of transporting this type of active agent with a very high specificity and, in inactive form, to diseased tissues or cells.

There is also a need for prodrugs of the dolastatin family of which the cytotoxicity is effectively expressed specifically at the level of the tumor microenvironment.

There is also a need for prodrugs of the dolastatin family of which the tumor efficacy does not require an excess amount of active agent, in order to prevent the occurrence of harmful side effects, in particular on healthy cells, tissues or organs.

SUMMARY OF THE INVENTION

The object of the present invention is precisely to meet these needs.

According to a first aspect, the present invention relates to a conjugate of general formula (I):

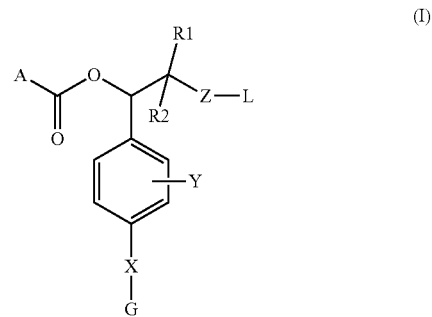

in which:
- A represents a radical of the dolastatin family or a derivative thereof,
- L represents a radical capable of reacting with an amino, hydroxyl or thiol function, and preferably a thiol function,
- G comprises and preferably represents a glucuronyl radical or a derivative thereof,
- Y represents H, or an electron-withdrawing radical, in particular chosen from $NO_2$, $CF_3$ and a halogen,
- $R^1$ and $R^2$ represent, independently of one another, H or a linear or branched, saturated or unsaturated $C_1$ to $C_{10}$ alkyl radical,
- Z represents a hydrocarbon-based spacer radical comprising, at each of its ends, covalent bond functions,
- X represents —O— or —$NR^3COO$—, with $R^3$ possibly representing a hydrogen atom or a linear or branched, saturated or unsaturated $C_1$ to $C_{10}$ alkyl radical, the bond with the G radical being provided by the oxygen atom (—O), an isomer thereof and/or a pharmaceutically acceptable salt thereof.

Unexpectedly, the inventors have in fact observed that a conjugate of general formula (I) and deriving from monomethyl auristatin E has an in vivo therapeutic efficacy that is significantly improved compared with non-functionalized monomethyl auristatin E.

Consequently, a conjugate in accordance with the invention proves to be particularly advantageous for the clinical treatment of cancers, from the viewpoint of its selectivity and its therapeutic dosage.

According to a second aspect, the present invention relates to a prodrug comprising at least one molecule of a conjugate of general formula (I) according to the invention, said molecule of said conjugate being linked via a covalent bond to an albumin molecule, which is in particular endogenous, or a derivative thereof.

As detailed hereinafter, the chemical structure of a conjugate according to the invention is most particularly suitable for its interaction with an albumin molecule, which is in particular endogenous, and more particularly a serum albumin molecule. Even more particularly, this interaction is in particular established in vivo, and is enabled by favoring an L radical of the type which has an affinity for the sulfur atom of the cysteine in position 34 of the endogenous albumin. This interaction with the sulfur atom of the cysteine may in particular come from a Michael reaction. The establishment of a covalent link between a conjugate molecule and an albumin molecule via a Michael reaction thus makes it possible to take advantage of the phenomenon of albumin accumulation in the tumor microenvironment and to obtain improved targeting of a conjugate according to the invention.

According to another aspect, the present invention also relates to a pharmaceutical composition comprising at least an effective amount of at least one conjugate of general formula (I) according to the invention, or a coupled form of said conjugate in which the latter is coupled with at least one albumin molecule and preferably a prodrug of general formula (VI), as defined according to the invention.

According to another aspect, the present invention relates to a conjugate of general formula (I), in accordance with the invention, for use thereof in the prevention and/or treatment of a cancer and/or of an inflammatory disease.

According to another aspect, the present invention relates to a coupled form of said conjugate in which the latter is coupled with at least one albumin molecule, and in particular a prodrug of general formula (VI) in accordance with the invention, for use thereof in the prevention and/or treatment of a cancer and/or of an inflammatory disease.

According to another aspect, the present invention relates to a composition, in accordance with the invention, for use thereof in the prevention and/or treatment of a cancer and/or of an inflammatory disease.

According to another aspect, the invention relates to a method for treating a cancer and/or an inflammatory disease, comprising the administration of a conjugate of general formula (I) in accordance with the present invention.

According to another aspect, the present invention also relates to a method for treating a cancer and/or an inflammatory disease, comprising the administration of a coupled form of said conjugate in which the latter is coupled with at least one albumin molecule and in particular a prodrug of general formula (VI) in accordance with the present invention.

Finally, according to a last aspect, the present invention also relates to a method for treating a cancer and/or an inflammatory disease, comprising the administration of a pharmaceutical composition in accordance with the present invention.

DETAILED DESCRIPTION OF THE INVENTION

Conjugates

Figure 1:
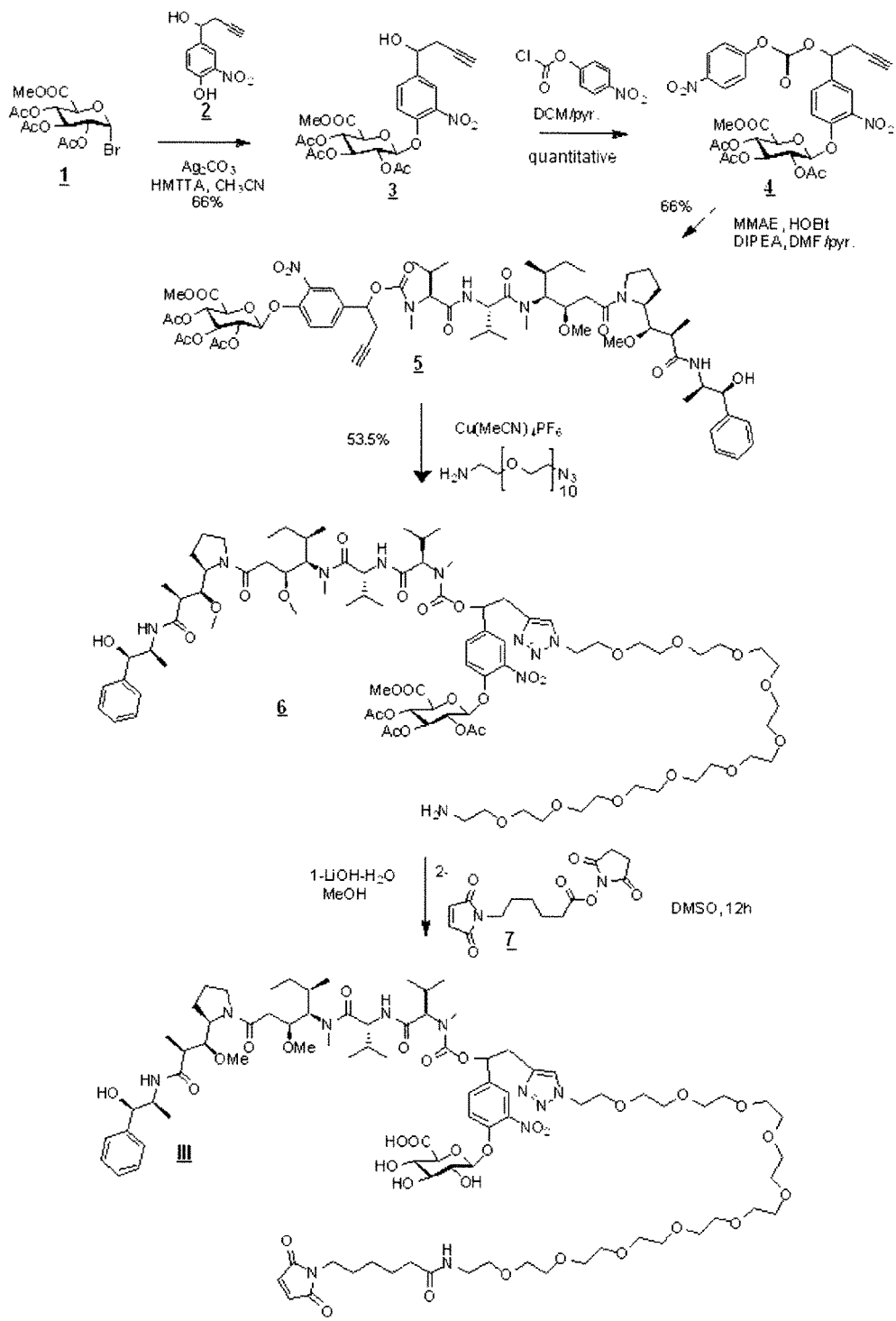
FIG. 1 illustrates a reaction scheme for synthesis of a conjugate of formula (III).

As specified above, a conjugate according to the invention corresponds to general formula (I):

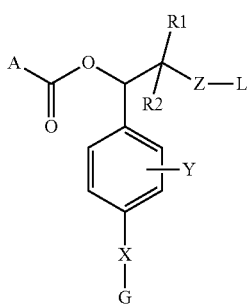

in which:
- A represents a radical of the dolastatin family or a derivative thereof,
- L represents a radical capable or reacting with an amino, hydroxyl or thiol function, and preferably a thiol function,
- G comprises and preferably represents a glucuronyl radical or a derivative thereof,
- Y represents H, or an electron-withdrawing radical, in particular chosen from $NO_2$, $CF_3$ and a halogen,
- $R^1$ and $R^2$ represent, independently of one another, H or a linear or branched, saturated or unsaturated $C_1$ to $C_{10}$ alkyl radical,
- Z represents a hydrocarbon-based spacer radical comprising, at each of its ends, covalent bond functions,
- X represents —O— or —$NR^3COO$—, with $R^3$ possibly representing a hydrogen atom or a linear or branched, saturated or unsaturated $C_1$ to $C_{10}$ alkyl radical, the bond with the G radical being provided by the oxygen atom (—O), an isomer thereof and/or a pharmaceutically acceptable salt thereof.

In the context of the present invention, a "derivative" of the dolastatin family refers to a compound which is structurally very related and which remains in possession of equivalent biological properties and in particular of a capacity to inhibit tubulin polymerization, in order to ultimately inhibit cell mitosis. It may in particular be a question of substitution or deletion derivatives.

In the context of the present invention, a "radical capable of reacting with an amino, hydroxyl or thiol function" refers to a radical, generally a hydrocarbon-based radical, which has a chemical function, or unit, capable of interacting with a free secondary amino, hydroxyl or thiol function and of thus establishing a covalent bond between a conjugate molecule and a distinct chemical entity carrying this function compatible with producing this covalent function. In the context of the present invention, this distinct chemical entity is more particularly a macromolecule naturally present in a living organism and advantageously an endogenous albumin molecule, like human serum albumin.

In the context of the present invention, an "electron-withdrawing radical" refers to the property of an atom or of a group of atoms of withdrawing electrons.

In the context of the present invention, an "isomer" refers to a molecule in which the position of at least two chemical groups on an asymmetric carbon is reversed compared with the reference molecule. In particular, a radical of the dolastatin family has numerous asymmetric carbons. Furthermore, the term "isomer" refers exclusively to a molecule capable of performing one or more identical or similar biological activity or activities compared with that of the reference molecule.

It is understood that the invention is intended to mean both isolated enantiomers and the corresponding racemic mixture.

In the context of the present invention, a "pharmaceutically acceptable salt" may be a salt of a conjugate, or of a pro-drug according to the invention, and of an alkali metal, of an alkaline-earth metal, or of ammonium, comprising the salts obtained with organic ammonium bases, or salts of a conjugate, or of a prodrug according to the invention, and of an organic or inorganic acid.

Salts which are more particularly suitable for the invention may be sodium, potassium, calcium, magnesium salts, quaternary ammonium salts such as tetramethylammonium or tetraethylammonium, and addition salts with ammonia and pharmaceutically acceptable organic amines, such as methylamine, dimethylamine, trimethylamine, ethylamine, triethylamine, ethanolamine or tris(2-hydroxyethyl)amine.

Salts of a conjugate, or of a prodrug according to the invention, and of an inorganic acid that are suitable for the invention may be obtained with hydrochloric acid, hydrobromic acid, sulfuric acid, nitric acid or phosphoric acid.

Salts of a conjugate, or of a prodrug according to the invention, and of an organic acid that are suitable for the invention may be obtained with carboxylic acids and sulfonic acids, such as formic acid, acetic acid, oxalic acid, citric acid, lactic acid, malic acid, succinic acid, malonic acid, benzoic acid, maleic acid, fumaric acid, tartaric acid, methanesulfonic acid, benzenesulfonic acid or p-toluenesulfonic acid.

Radical of the Family of Dolastatins and Derivatives Thereof (A Radical)

The dolastatin family represents a class of compounds having a structure of at least 4 amino acids, at least 3 of which are specific thereto, i.e. different from the 20 amino acids most commonly found naturally.

Reference may in particular be made to document WO 2004/010957, the content of which is incorporated by way of reference, which describes compounds in accordance with those that are suitable for the present invention.

In one particularly preferred embodiment of the invention, A represents a radical which derives from dolastatin 10, from auristatin PE, from auristatin E, from monomethyl auristatin E and derivatives thereof, preferably a radical which derives from monomethyl auristatin E or a derivative thereof.

The structural difference between dolastatin 10 and the synthetic compounds of the auristatin subfamily lies in particular in the substitution of the aminothiazolephenethyl group in the C-terminal position of dolastatin 10, by a norephedrine unit in the case of auristatin PE, of auristatin E or of monomethyl auristatin.

In the context of the present invention, and in one particularly preferred embodiment, the radical of the dolastatin family is advantageously chosen from monomethyl auristatin E (MMAE) and a derivative thereof.

For the purposes of the invention, a derivative of dolastatin 10, of auristatin PE, of auristatin E or of monomethyl auristatin E has a chemical structure very related to at least one of its active agents and has antimitotic properties attributed to the compounds of the dolastatin family.

Its structural difference(s) may in particular be, for example, a substitution on at least one side chain of at least one of the four amino acids of which it is composed. This substitution may be carried out so as to contain or represent a linear, cyclic and/or branched alkyl group, an aryl group, a heterocycle or a carbocycle.

This structural difference may also consist of a modification of a dolostatin 10, auristatin PE or auristatin E molecule, for example at the level of its tertiary amine in the N-terminal position, so as to render this function compatible with the establishment of a covalent bond with the linker arm under consideration.

It is part of the general knowledge of those skilled in the art to select the modifications most suitable for these purposes.

L Radical

As emerges from the aforementioned, the conjugates according to the invention have the originality of being doubly functionalized and in particular of being functionalized with a radical capable of conferring on them an ability to interact with a macromolecule, particularly an endogenous macromolecule, and even more particularly a serum albumin molecule.

Since biological macromolecules, and in particular endogenous albumin, are today known to accumulate via the "EPR" ("Enhanced Permeability and Retention") effect in the microenvironment of solid tumors, the in situ coupling of a conjugate according to the invention with an endogenous albumin molecule makes it possible to target the coupled entity thus formed, also called prodrug, into the tumor microenvironment and thus to overcome the lack of selectivity of the free forms of dolastatin derivatives. It should be noted that such an "EPR" effect applies to the microenvironment of inflamed tissues.

It should also be noted that this principle of targeting diseased tissues and/or cells by means of a macromolecule has already been proposed for doxorubicin (Legigan et al. 2012, J. Med. Chem). Nevertheless, while this prodrug has an improved half-life compared with a prodrug functionalized with a single glucuronyl radical, it does not make it possible to obtain a gain efficacy compared with non-functionalized doxorubicin, which has the drawback of being not very effective and therefore of requiring high doses which are not very compatible with a treatment that can be tolerated by a subject.

As will be detailed hereinafter (example 2 and FIG. 2), a conjugate in accordance with the invention and administered parenterally, proves, on the other hand, to have a significantly improved efficacy compared with that of a compound of the dolastatin family taken in an isolated state, i.e. non-functionalized.

In the case where the prodrug envisaged is intended to be generated in vivo, i.e. by establishing a covalent bond between a conjugate of general formula (I) and a macromolecule such as albumin, it is particularly advantageous to favor, at the level of the conjugate, an L radical comprising a unit capable of interacting with a free thiol function, in order to favor the affinity of the conjugate for serum albumin.

Such a unit makes it possible to establish, in vivo, a covalent bond with a free thiol function (—SH) of the serum albumin, in particular with interaction with the free thiol function (—SH) of the cysteine in position 34. This covalent bond, i.e. a thioether bond, is advantageously produced by a Michael reaction.

Thus, in one particularly preferred embodiment, the invention relates to a conjugate in which L represents a unit of maleimidocaproyl type.

However, in the case where it is envisaged to synthesize the prodrug prior to its administration, the conjugate of formula (I) may represent an L radical comprising a unit capable of reacting with an amino (—NH$_2$), hydroxyl (—OH) or thiol (—SH) function. These reactive functions make it possible to produce covalent bonds between, on the one hand, the conjugate of formula (I), via the L radical, and, on the other hand, a macromolecule or a fragment of a macromolecule.

The choice of the unit carried by the L radical and capable of reacting with an amino (—NH$_2$), hydroxyl (—OH) or thiol (—SH) function is made from the viewpoint of the nature of the function present on the macromolecule to be coupled and is clearly part of the competence of those skilled in the art.

Glucuronyl Radical and Derivatives Thereof (G Radical)

In the context of the present invention, the glucuronyl radical (G radical) is dedicated to being removed enzymatically, in order to thus provide an intramolecular rearrangement of the linker arm linking it to the molecule of the dolastatin family and, consequently, results in release of this active molecule (A radical).

Furthermore, a glucuronyl radical according to the invention, which is enzymatically hydrolyzable, may confer a tissue and/or cell specificity on the conjugates and prodrugs in accordance with the present invention.

It is known that β-glucuronidase is an enzyme naturally present at a high concentration in the neighborhood of many tumors. The conjugates and prodrugs of the invention comprising a glucuronyl group may therefore be advantageously activated at the extracellular level, during prodrug monotherapies (or PMTs). In the context of the invention, the term "activation" refers to the release at the tumor site, for example, of the radical of the family of dolastatins, which are thus capable of performing their antimitotic biological activity.

Moreover, β-glucuronidase is a lysosomal enzyme which is present in most malignant cells. Thus, the activation of a glucuronylated prodrug by a β-glucuronidase may be optionally carried out in the intracellular medium after internalization by endocytosis.

According to one implementation variant, an enzymatically hydrolyzable glucuronyl radical that is suitable for the invention may in particular be a polysaccharide comprising from 2 to 20, in particular from 3 to 10, and more particularly from 4 to 6 glucuronyl units or derivatives thereof.

In the context of the present invention, a "derivative" of the glucuronyl radical refers to a compound which is structurally very related and which remains in possession of equivalent biological properties and in particular of a capacity to be the enzymatic substrate of a β-glucuronidase. It may in particular be a question of derivatives of substitution or deletion of one or more hydroxyl (—OH) group(s) or of the carboxylic (—COOH) group.

This glucuronyl radical may advantageously interact with the linker arm under consideration according to the invention via one of its hydroxyl functions and the covalent link represented by X is then an oxygen atom.

As previously mentioned, —X-G may also be represented by a carbamoyl-glucuronide derivative.

Linker Arm Between the a, L and G Radicals

As previously stated, the conjugates according to the invention have a linker arm dedicated, on the one hand, to combining, in the form of one and the same molecule, the various functionalities represented by the A, L and G radicals and, on the other hand, to allowing the release of the active molecule (A radical) in response to enzymatic hydrolysis of the glucuronyl (G radical).

What is more, this linker arm is such that it:
- does not impair the anti-cancer and/or anti-inflammatory properties carried by the compound of the dolastatin family (A radical),
- does not compromise the labile properties of the glucuronyl radical (G radical), intended to be cleaved by a β-glucuronidase in the microenvironment of the tissue to be treated, consequently allowing the rearrangement of the conjugated molecule and the release of the A radical carrying the active ingredient,
- allows the interactions between a molecule of a conjugate of general formula (I) and a macromolecule, in other words maintains the accessibility of the function capable of reacting with the amino, hydroxyl or thiol function of the endogenous albumin, and
- does not affect the half-life of the conjugate in the organism in which it may be administered.

A linker arm that is particularly suitable for carrying out the present invention is in particular described in document WO 2011/145068, which is moreover incorporated by way of reference.

This linker arm is in particular in accordance with formula (II) below:

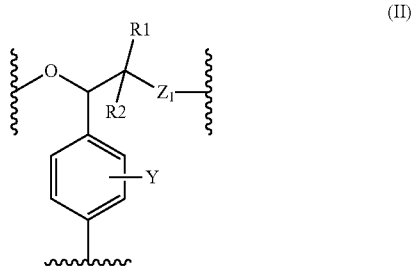

(II)

The $R^1$, $R^2$ and Y groups are as defined above.

$Z^1$ represents an L-click linker function, as detailed hereinafter and which is part of the spacer radical Z of the conjugate of formula (I).

In one particularly preferred embodiment of the invention, Y represents $NO_2$ in the ortho position of X, and $R^1$ and $R^2$ represent H.

Spacer Radical Z

As stated above, the linker arm is connected via the Z' function to the rest of the Z radical of the conjugate of formula (I) described in the present invention.

Thus, Z is represented by the sequence —$Z^1$—$Z^2$—$(Z^3)_m$—, for which:
- m represents 0 or 1,
- $Z^1$ represents an L-click linker function between the carbon carrying the $R^1$ and $R^2$ functions, and the $Z^2$ function, $Z^2$ represents a linear or branched, saturated or unsaturated $C_1$-$C_{10}$ alkylene group, optionally interrupted with one or more heteroatoms chosen from O or N, a glycosyl radical, an O—(CHR$^4$—CHR$^5$—O—)$_p$ or N—(CHR$^4$—CHR$^5$—O—)$_p$ radical in which p represents a natural integer ranging from 1 to 20, and $R^4$ and $R^5$ represent, independently of one another, H or $CH_3$, with the proviso that $R^4$ and $R^5$ do not simultaneously represent $CH_3$, a group derived from an amino acid or from a peptide, or a combination of these groups, one end of $Z^2$ producing a covalent bond with L, either directly via an ether function, or indirectly via a $Z^3$ function, $Z^3$, if present, represents a function of ester, amide, ether, carbamate or carbonate type between $Z^2$ and the L radical.

In the context of the invention, an "L-click linker function" refers to the product of the reaction of 2 functions suitable for click chemistry. Click chemistry groups together a set of reaction processes well known to those skilled in the art and makes it possible to simply and rapidly produce covalent bonds between two reactive or functionalized functions. In this regard, reference may in particular be made to the review by Kolb et al. (2004, Angew. Chem. Int. Ed.).

It is within the competence of those skilled in the art to choose a $Z^1$ function suitable for establishing a covalent bond with the reactive function activatable by click chemistry.

According to one preferred embodiment, $Z^1$ may be the result of the reaction of 2 reactive functions activatable by click chemistry is chosen from —C≡CR$^6$, —$N_3$, —SH, —C═$CH_2$, cyclooctynes, maleimide, —$SO_2N_3$ or —COSR$^6$, with $R^6$ representing H or a linear or branched, saturated or unsaturated $C_1$ to $C_{10}$ alkyl radical.

According to another preferred embodiment, $Z^1$ may be the result of the reaction of 2 reactive functions activatable by click chemistry is chosen from —C≡CH, —$N_3$, —SH, —C═$CH_2$, cyclooctynes, maleimide, —$SO_2N_3$ oR —COSR$^6$, with $R^6$ as described above.

According to one more particularly preferred embodiment, $Z^1$ may be the result of the reaction between a reactive function —C≡CH and a reactive function —$N_3$.

In one particularly preferred embodiment of the invention, $Z^2$ represents an O—(CHR$^4$—CHR$^5$—O—)$_p$ radical, in which p represents a natural integer ranging from 1 to 20, and $R^4$ and $R^5$ represent, independently of one another, H or $CH_3$, with the proviso that $R^4$ and $R^5$ do not simultaneously represent $CH_3$, a group derived from an amino acid or from a peptide, or a combination of these groups.

In another preferred embodiment of the invention, $Z^2$ represents an O—($CH_2$—$CH_2$—O—)$_p$ radical, in which p represents a natural integer ranging from 1 to 20.

In another particularly preferred embodiment of the invention, $Z^2$ represents an O—($CH_2$—$CH_2$—O—)$_{10}$ radical.

Thus, in one particular embodiment, the present invention relates to a conjugate of formula (III) below:

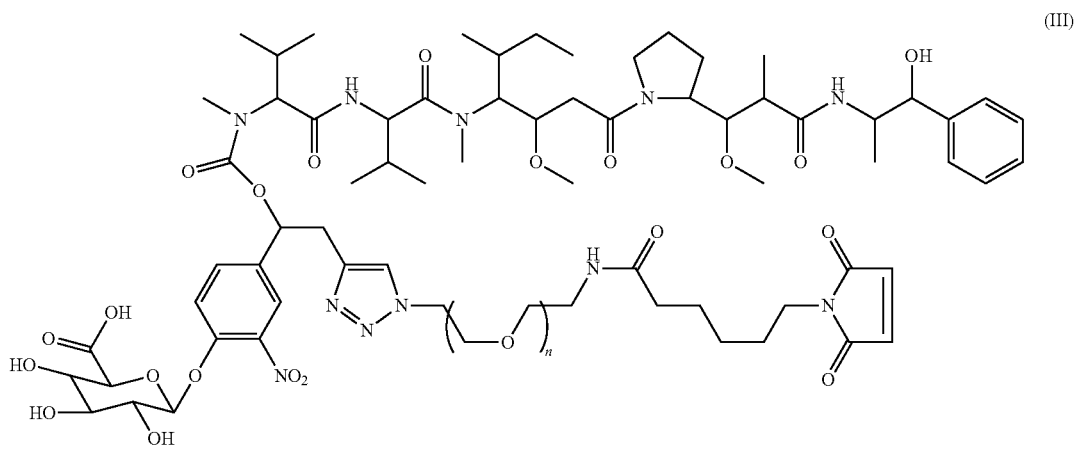
(III)

an isomer thereof and/or a pharmaceutically acceptable salt thereof.

Synthesis of the Conjugates in Accordance with the Present Invention

A conjugate of general formula (I), in accordance with the present invention, may be synthesized from a molecule which is a precursor of the linker arm of formula (II), as represented by general formula (IV) below:

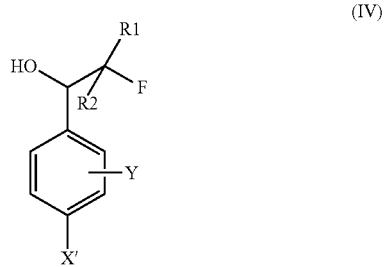
(IV)

in which:

X' may represent —OH or —NR³COOH, with R³ possibly representing a hydrogen atom or a linear or branched, saturated or unsaturated $C_1$ to $C_{10}$ alkyl radical, Y may represent H, or an electron-withdrawing group, in particular chosen from $NO_2$, $CF_3$ and a halogen, $R^1$ and $R^2$ may represent, independently of one another, H or a linear or branched, saturated or unsaturated $C_1$ to $C_{10}$ alkyl radical, F represents a reactive function activatable by click chemistry.

This type of compound is in particular described in publication WO 2011/145068, which is moreover incorporated by way of reference.

The grafting of the various groups or radicals present is part of the general knowledge of those skilled in the art.

In one particularly preferred embodiment, this compound is the compound of formula (V) below:

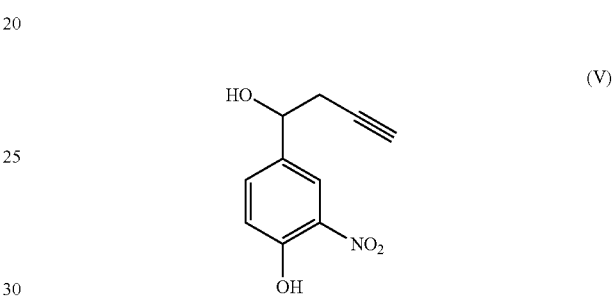
(V)

It is understood that those skilled in the art, by virtue of their general knowledge, may determine the order of the reactions to be carried out in order to form, from such a compound, a conjugate of general formula (I).

The reactions which make it possible successively to establish a covalent bond between a compound of formula (IV) or (V) and i) a glucuronyl radical (G radical), ii) a radical of the dolastatin family (A radical), iii) a hydrocarbon-based spacer radical (Z) are well known to those skilled in the art and do not present any particular implementation difficulties. Moreover, such reactions are, for example, described in particular in the documents Legigan et al. (2013, Eur. J. Med. Chem.) and Legigan et al. (2012, J. Med. Chem). If necessary, protection reactions with regard to alcohol (—OH) functions, amine (—NH₂) functions or the like are capable of being considered prior to the coupling reactions.

The reaction which makes it possible to establish a covalent bond between a hydrocarbon-based spacer radical (Z radical) and a radical capable of reacting with a thiol function (L radical) is in particular described in the document Legigan et al. (2012, J. Med. Chem).

The conditions suitable for carrying out these reactions, the purification methods, and the methods for evaluating the purity of the compounds synthesized are part of the general knowledge of those skilled in the art.

Prodrugs

According to another of its aspects, the invention relates to a prodrug comprising at least one conjugate molecule according to the invention, bonded via a covalent bond to at least one albumin molecule or a derivative thereof.

For the purposes of the invention, "prodrug" refers to a molecule capable of transporting, in inactivated form, a compound of the dolastatin family within an organism, and of releasing said compound in an organ, a tissue or cells which is (are) specifically targeted, under the action of a β-glucuronidase.

More specifically, such a prodrug advantageously corresponds to general formula (VI) below:

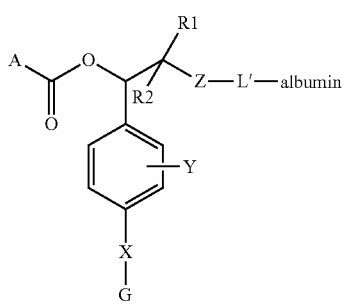 (VI)

for which the A, G, X, Y, Z, $R^1$ and $R^2$ radicals are as defined above.

The L' unit, for its part, derives from the reaction between, on the one hand, an L radical comprising a unit capable of reacting with a free amino, hydroxyl or thiol function and in particular with a free thiol function carried by a macromolecule, advantageously an albumin molecule, even more advantageously serum albumin.

In the context of the present invention, the prodrug may be formed in vivo or in vitro with a macromolecule, preferably with an albumin molecule.

Thus, an endogenous or exogenous albumin, and in particular a human serum albumin, a recombinant albumin or else a fragment of an albumin, may be envisaged.

In a first preferred embodiment of the invention, the covalent bonding between a molecule of the conjugate, as described by the present invention, and a molecule of endogenous albumin, in particular a molecule of human serum albumin, or a derivative thereof, is carried out in vivo.

In one more particularly preferred embodiment, a prodrug according to the invention comprises at least one molecule of conjugate according to the invention linked via a thioether bond to the sulfur of the cysteine in position 34 of a molecule of endogenous albumin.

It has in fact been shown that a covalent bond establishes spontaneously in vivo, for example, between, on the one hand, a compound carrying a radical capable of reacting with a thiol function and the thiol function of the cysteine in position 34 of human serum albumin (Kratz et al. 2002, J. Med. Chem.).

According to one particularly preferred embodiment, the invention also relates to a prodrug, the formula of which is formula (VII) below:

an isomer thereof and/or a pharmaceutically acceptable salt thereof.

According to a particular second embodiment, a prodrug according to the invention may also be formed in vitro by at least one conjugate molecule linked via a covalent bond to an albumin molecule, a recombinant albumin molecule or a fragment of an albumin molecule or a derivative thereof.

For the purposes of the invention, it is important that the "fragment of an albumin molecule" denotes a fragment of an albumin molecule having a size sufficient to guarantee satisfactory bioavailability, permeability with respect to tumor tissues and impermeability with respect to the endothelial barrier of healthy tissues, of the prodrug thus generated.

In this particular embodiment, the in vitro coupling between a conjugate of general formula (I), via its L radical, and an albumin molecule, a recombinant albumin molecule or a fragment of an albumin molecule may be carried out with a free and complementary reactive function present on the albumin molecule, the recombinant albumin molecule or the fragment of an albumin molecule.

In one particular embodiment, the fragment of an albumin molecule may comprise the cysteine corresponding to the cysteine in position 34 of the endogenous albumin sequence.

Against all expectations, the coupling of a conjugate of general formula (I) and of an albumin molecule does not in any way affect the ability of the prodrug thus formed to:
- be transported and targeted specifically into the microenvironment of the tissue to be treated,
- be cleaved in the microenvironment of the tissue to be treated by a β-glucuronidase, and
- undergo, after cleavage of the glucuronyl radical, a rearrangement of the linker arm so as to release the radical representing a compound of the dolastatin family.

Furthermore, the coupling between a conjugate of general formula (I), via its L radical, and the amino, hydroxyl or thiol function of an albumin molecule, in particular an endogenous albumin molecule, does not in any way affect the ability of the compound of the dolastatin family thus released to perform its biological activity, i.e. its antimitotic activity.

Finally, the coupling between a conjugate of general formula (I), via its L radical, and the amino, hydroxyl or thiol function of an albumin molecule, in particular an endogenous albumin molecule, limits the elimination of the prodrug by the kidneys. The half-life in the blood of a

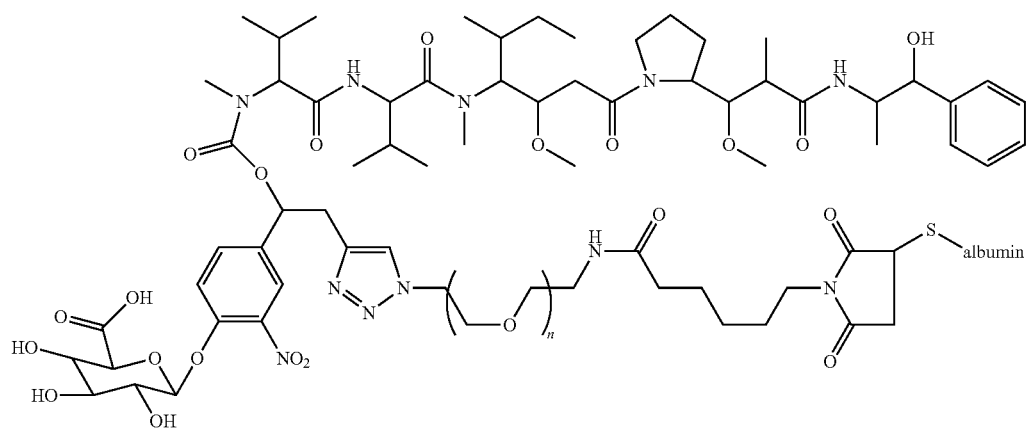 (VII)

prodrug according to the invention is thus increased in comparison with that of a prodrug represented by a compound of the dolastatin family functionalized with a glucuronyl radical.

In another embodiment of the invention, the albumin molecule, or albumin fragment, of the prodrug may also be modified, in particular by glycosylation or by pegylation.

Compositions, Uses and Methods of Treatment According to the Invention

According to another aspect, the present invention relates to a pharmaceutical composition comprising at least an effective amount of at least one conjugate or one prodrug, as previously defined.

These pharmaceutical compositions may be in a solid or liquid state and may be in any of the pharmaceutical forms commonly used in human and/or veterinary medicine, for example in the form of simple or sugar-coated tablets, of pills, of lozenges, of gel capsules, of drops, of granules, of injectable preparations, of ointments, of creams or of gels.

These pharmaceutical compositions may be prepared according to the usual methods. The active ingredient may therein be incorporated into excipients normally used in these pharmaceutical compositions, such as talc, gum arabic, lactose, starch, magnesium stearate, cocoa butter, aqueous or nonaqueous vehicles, fatty substances of animal or vegetable origin, paraffin derivatives, glycols, the various wetting agents, dispersants or emulsifiers, or preservatives.

The invention also relates to a conjugate of general formula (I), a prodrug of general formula (VI) or a pharmaceutical composition, as defined in the present invention, for use thereof in the prevention and/or treatment of a cancer and/or of an inflammatory disease.

The invention also relates to a method for treating a cancer and/or an inflammatory disease, comprising the administration of a conjugate of general formula (I), of a prodrug of general formula (VI) or of a pharmaceutical composition, in accordance with the present invention.

The invention also relates to a method for treating a cancer and/or an inflammatory disease, comprising the administration of a conjugate of formula (I), of a prodrug of general formula (VI) or of a pharmaceutical composition according to the invention, in combination with another treatment chosen from a group comprising chemotherapy, radiotherapy, treatment with at least one anti-inflammatory agent, and a combination thereof.

Cancer

A conjugate of general formula (I), a prodrug of general formula (VI) or a pharmaceutical composition according to the present invention may be employed, for use thereof in the prevention and/or treatment of a solid cancer, preferably chosen from a group comprising a neuroblastoma, a glioblastoma, an osteosarcoma, a retinoblastoma, a soft tissue sarcoma, cancer of the central nervous system, a nephroblastoma, lung cancer, breast cancer, prostate cancer, colorectal cancer, thyroid cancer, cervical cancer, endometrial cancer, ovarian cancer, kidney cancer, liver cancer, brain cancer, testicular cancer, pancreatic cancer, bone cancer, skin cancer, cancer of the small intestine, stomach cancer, pleural cancer, esophageal cancer, cancer of the larynx and bladder cancer.

In one particular embodiment, the solid cancer is chosen from a group comprising pancreatic cancer, lung cancer and breast cancer.

In one particular embodiment, a conjugate of general formula (I), a prodrug of general formula (VI) or a pharmaceutical composition according to the present invention may be employed, for use thereof in the prevention and/or treatment of metastases.

Inflammatory Diseases

With regard to inflammatory diseases, there are in particular chronic pathological conditions of the intestine, or rheumatoid pathological conditions.

Administration Modes

A conjugate of general formula (I), a prodrug of general formula (VI) or a pharmaceutical composition, as described in the present invention, may be administered orally, parenterally (subcutaneously, intravenously or intramuscularly) or locally by topical application to the skin and the mucous membranes.

A subject of the present invention is also the use of conjugates, of prodrugs or of pharmaceutical compositions, as defined above, for preparing medicaments.

Such medicaments may be used alone or in combination.

Conjugates, prodrugs or pharmaceutical compositions in accordance with the present invention may in particular be administered alone or in combination with chemotherapy or radiotherapy or else in combination, for example, with other therapeutic agents, in particular anticancer agents and antimitotics, but also in combination with anti-inflammatory agents.

A dosage suitable for the invention may be determined according to a routine approach normally used in the art. The adjustment of said dosage is clearly part of the general competence of those skilled in the art.

It is in fact dependent, in particular, on the weight, age and sex of the individual to be treated, and on the state of progression of the disease to be treated.

EXAMPLES

Example 1

Synthesis of a Conjugate of Formula (III) (See FIG. 1)
1) Synthesis of Compound 1

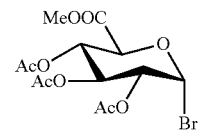

17.9 g (48 mmol; 1 eq.) of peracetylated glucuronide are suspended in 36 ml of HBr at 33% in acetic acid. After stirring for 4 h, the starting compound is entirely consumed. The reaction medium is then poured into a mixture of water and ice and the aqueous phase obtained is extracted three times with dichloromethane. The organic phase is then neutralized with a saturated NaHCO$_3$ solution, dried over MgSO$_4$, and evaporated. 3 ml of absolute ethanol are added to the crude product and then the mixture is stored overnight in the refrigerator. The precipitate formed is collected by filtration and then washed with petroleum ether. After drying under vacuum, 17.4 g (43.8 mmol; yield=91%) of compound 1 are isolated in the form of a beige solid.

2) Synthesis of Compound 2

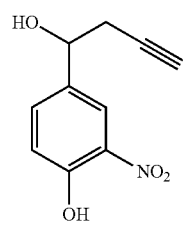

In a 250 ml three-necked flask equipped with a condenser and a dropping funnel, 648 mg (24 mmol; 6.25 eq.) of aluminum and a catalytic amount of $HgCl_2$ are covered with 10 mL of anhydrous THF. 2, ml (24 mmol; 6.25 eq.) of a solution of propargyl bromide at 80% in toluene are added dropwise. The reaction begins when a release of heat and blackening of the solution are observed. When the addition is finished, the mixture is refluxed for 6 hours. The solution is cooled to 0° C. and a solution of 650 mg (3.84 mmol; 1 eq.) of 4-hydroxy-3-nitrobenzaldehyde in 5 ml of anhydrous THF is added dropwise. After stirring for 30 minutes, the aldehyde has totally disappeared and the reaction is hydrolyzed with 10 ml of a 1N HCl solution and then extracted three times with ethyl acetate. The organic phase is dried over $MgSO_4$ and then evaporated to give a brown oil which is purified by flash chromatography (Eluant: 70/30 PE/EtOAc). Compound 2 is then obtained in the form of a yellow oil contaminated with traces of products resulting from the Wurtz reaction. A basic extraction makes it possible to remove these impurities. For this, the oil is dissolved in 30 ml of dichloromethane. The organic phase is extracted three times with a 1N NaOH solution. The aqueous phase obtained is acidified with a concentrated HCl solution and then extracted three times with chloroform to give, after evaporation, compound 2 (754 mg; 3.6 mmol) in the form of a brown oil, with a yield of 94%.

3) Synthesis of Compound 3

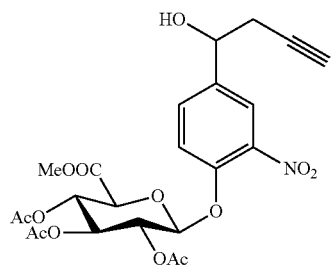

33.7 g (122.25 mmol; 3.7 eq.) of $Ag_2CO_3$ are suspended in 33 ml of acetonitrile and 6.3 ml (23.12 mmol; 0.7 eq.) of HMTTA are added. The mixture is left to stir in the dark for 2 h. 4.56 g (22.03 mmol; 1 eq.) of compound 2 and 13.10 g (33.04 mmol; 1.5 eq.) of compound 1 are added in solution in 20 ml of acetonitrile. The mixture is left to stir for 4 h and then water is added. This aqueous phase is extracted three times with ethyl acetate. The organic phase is washed three times with a 1M HCl solution, dried over $MgSO_4$ and evaporated. Purification of the reaction crude by flash chromatography (Eluant PE/EtOAc 60/40; 50/50; 40/60) makes it possible to obtain 7.62 g (14.56 mmol; yield=66%) of compound 3 in the form of a white solid (2 diastereoisomers).

4) Synthesis of Compound 4

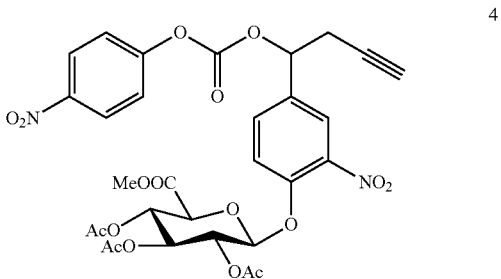

180 mg (0.34 mmol; 1 eq.) of benzyl alcohol and 140 mg (0.68 mmol; 2 eq.) of para-nitrophenol chloroformate are dissolved in 3.5 ml of anhydrous dichloromethane. 70 μl of pyridine (0.87 mmol; 2.5 eq.) are added dropwise at 0° C. After stirring for 1 h at ambient temperature, the starting product was entirely consumed. The reaction is hydrolyzed with a saturated $NaHCO_3$ solution. The organic phase is extracted with dichloromethane. The resulting organic phases are dried and evaporated to dryness. Flash chromatography (60/40 PE/EtOAc) makes it possible to isolate 235 mg (0.343 mmol) of compound 4 in the form of a white solid with a quantitative yield.

5) Synthesis of Compound 5

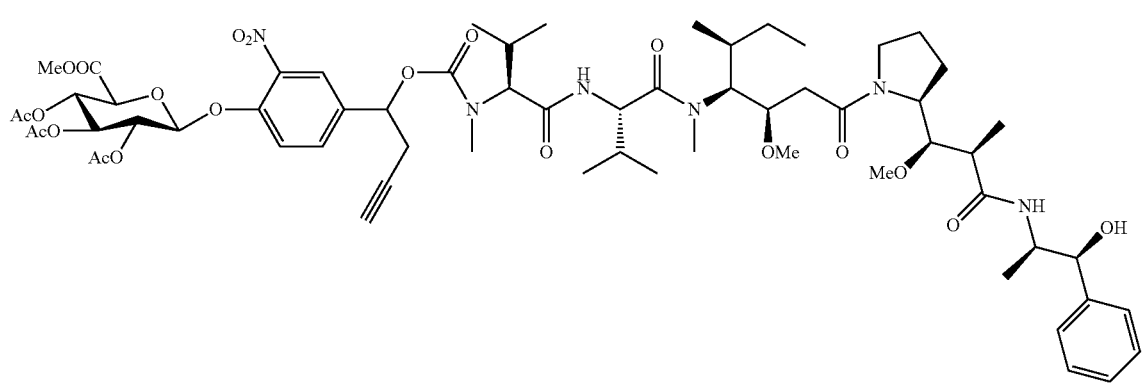

Compound 4 (57.5 mg; 0.0835 mmol) and MMAE (60 mg; 1 eq.) are dissolved in 2 ml of a DMF/pyridine mixture (8/2). 11.3 mg of HOBt (0.0835 mmol; 1 eq.) and 17 µl of DIPEA (0.1 mmol; 1.2 eq.) are added. The stirring is maintained for 36 h at ambient temperature. The solvent is removed under vacuum and the residue is purified by flash chromatography (Eluant: DCM/MeOH 3%-5%). 70 mg of compound 5 are obtained (0.055 mmol; 66%) in the form of a white solid.

6) Synthesis of Compound 6

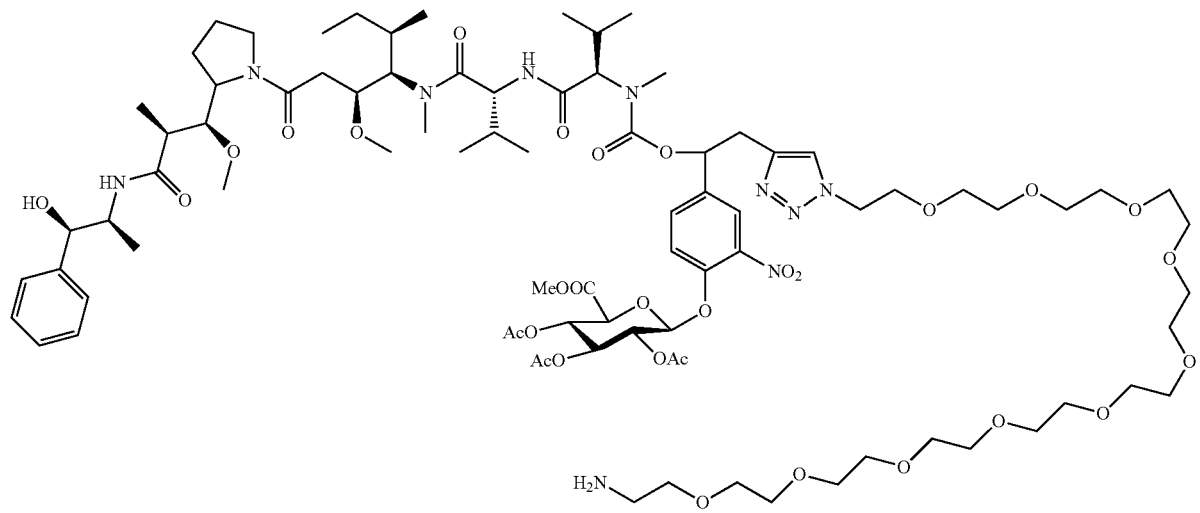

Compound 5 (70 mg; 0.055 mmol) is dissolved in anhydrous DCM (2.8 ml) in the presence of the azide of formula $NH_2-(CH_2)_2-(O-CH_2-CH_2)_{10}-N_3$ (37.8 mg; 0.0717 mmol; 1.3 eq.). 30 mg (0.08 mmol; 1.5 eq.) of $Cu(MeCN)_4PF_6$ are added and the mixture is left to stir for 20 h at ambient temperature under a nitrogen atmosphere. A solution of disodium EDTA (350 mg in solution in 5.2 ml of a 0.2 M phosphate buffer solution) is added and the stirring is maintained for 5 h. The mixture is extracted 3 times with dichloromethane. The organic phases are dried over $MgSO_4$, filtered and evaporated under vacuum. The crude product obtained is purified on preparative plates (Eluant DCM/MeOH, 2-5%). The corresponding compound 6 (53 mg; 0.029 mmol) is isolated with a yield of 53.5%.

7) Synthesis of the Compound of Formula (III)

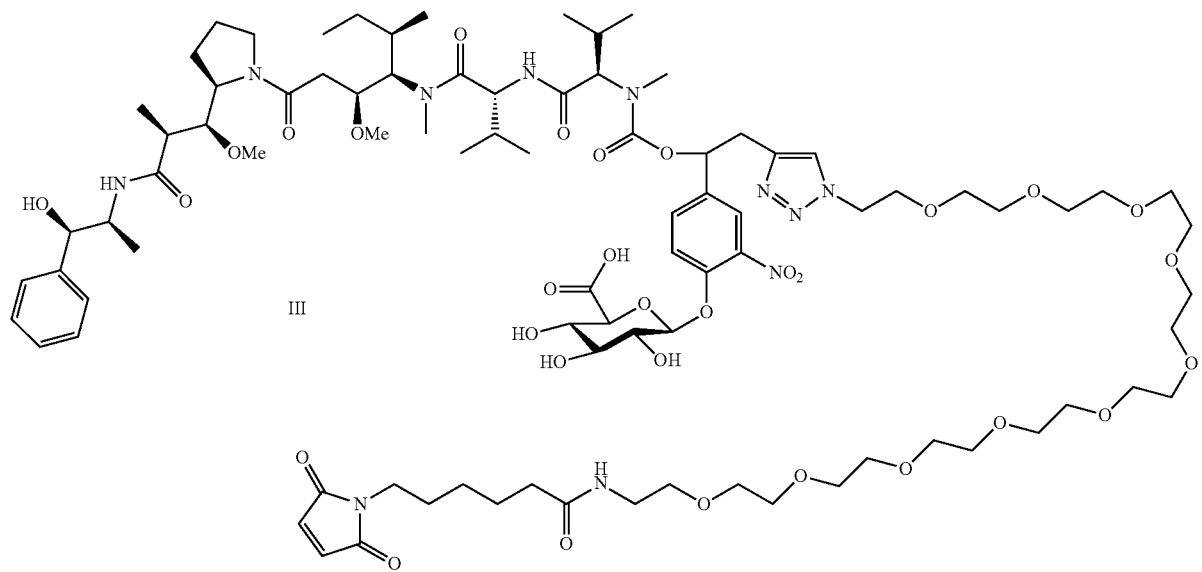

(III)

Compound 6 (53 mg; 0.029 mmol) is dissolved in MeOH (2.2 ml) at 0° C. A solution of $LiOH.H_2O$ (10.6 mg; 0.259 mmol) in 2.2 ml of $H_2O$, precooled to 0° C., is added dropwise. The reaction medium is kept stirring at this temperature. TLC monitoring indicates the disappearance of the starting product after 15 minutes. The medium is then neutralized by adding IRC-50 resin. After 30 minutes, the resin is filtered off and the reaction medium is evaporated under vacuum. The crude product is directly taken up in DMSO (0.7 ml) in the presence of compound 7 (1.2 eq.; 11 mg). The stirring is maintained for 12 h at ambient temperature. After evaporation of the solvent under vacuum, the reaction crude is purified by semi-preparative HPLC. 18 mg of conjugate of formula (III) are thus isolated (0.0097 mmol) with a purity greater than 95% and an overall yield of 33% (calculated over 3 click-deprotection semi preparative HPLC purification steps).

HRMS (ESI): $C_{88}H_{41}N_{11}O_{31}$ [M+2H]2+: theoretical: 923.9638; found: 923.9892.

8) HPLC Monitoring

The reaction monitoring and the compound analysis were carried out on a Dionex Ultimate 3000 HPLC apparatus equipped with a quadruple wavelength UV detector and with a Dionex Acclain® 120 column (C18, 5 μm, 120 Å) in a compartment thermostatted at 30° C. The chromatograms are recorded at 220 and 254 nm. The integration is provided by the Chromeleon software version 6.80 SP1 Build 2238. The eluants are composed of A ($H_2O$+TFA 0.2%), B ($CH_3CN$).

Example 2

Evaluation of the Therapeutic Efficacy of the Conjugate of Formula (III) In Vivo on a Murine Model of Human Pancreatic Cancer 1) Materials and Methods a) Animals Used The therapeutic efficacy of the conjugate of formula (III), as synthesized according to the reaction protocol described in example 1, was evaluated on 6-week-old female Swiss Nude mice (Charles River France Laboratories, l'Arbresle). The animals were acclimatized for 7 days in the laboratory before the experiment. The mice were housed in plastic cages equipped with filtering lids (HEPA filter), in a ventilated cage rack, housed at a temperature of 20±2° C. with a light/dark cycle of 12/12 hours, with free access to water and food ad libitum.

b) Orthotopically Grafted Human Pancreatic Tumor of Mia Paca Type

The Mia Paca 2 cells originate from a pancreatic adenocarcinoma from a 65-year-old man. The Mia Paca 2 pancreatic cancer cell line was supplied by the American Type Culture Collection (Rockville, Md.). These cells were chosen since they make it possible to generate tumors of hypoxic nature, reflecting the clinical pathological situation.

These cells were modified to express the luciferase gene (Mia PaCa 2-Luc). The cells were cultured in 75 $cm^3$ flasks and maintained in a humidified incubator at 37° C. in 5% $CO_2$ with Dulbecco's Modified Eagle Medium (DMEM) supplemented with 10% of fetal calf serum, 2.5% of horse serum, 1% of L-glutamine and 1% of penicillin and streptomycin.

For the implantations, the abdomens of the mice were disinfected with an iodinated povidone solution (Betadine®, ASTA Medica, Belgium). A 1 cm incision was made in the upper left quadrant of the abdomen. The end of the tail of the pancreas was seized and the pancreas and also the spleen were gently externalized in a lateral direction so as to be fully exposed. The needle was inserted into the tail of the pancreas and positioned just in the region of the head of the pancreas. $2\times10^6$ Mia PaCa 2-Luc cells in 50 μl of PBS were slowly injected using a 27-caliber needle. The spleen was then put back into the appropriate position in the abdomen and the skin and the peritoneum were sutured with a 5.0-diameter resorbable thread. The animals' pain was treated with an opioid analgesic (microgranules of Skenan LP 10 mg, Bristol-Myers Squibb).

c) Treatment Modes

The mice (6 animals per group) received a treatment 7 days after the tumor implantations. The intravenous injections were carried out once a week for 2 weeks with doses of 2 mg/kg and 4 mg/kg of bifunctionalized MMAE (conjugate of formula (III), $D_7$ and $D_{14}$). The control groups were treated either with MMAE alone with a dose of 0.3 mg/kg, or with the excipient consisting of a mixture of DMSO and PBS (5%/95%; control).

The evolution of the tumor volume was monitored by echography. The measurements were carried out with the VisualSonics Vevo™ 2100 system, which is a high-resolution in vivo imaging system (VisualSonics™ Inc., Toronto, Canada), on days 3, 7, 9, 11, 14, 16, 18, 21, 23, 28, 38, 52, 66 and 78.

2) Results

Figure 2:
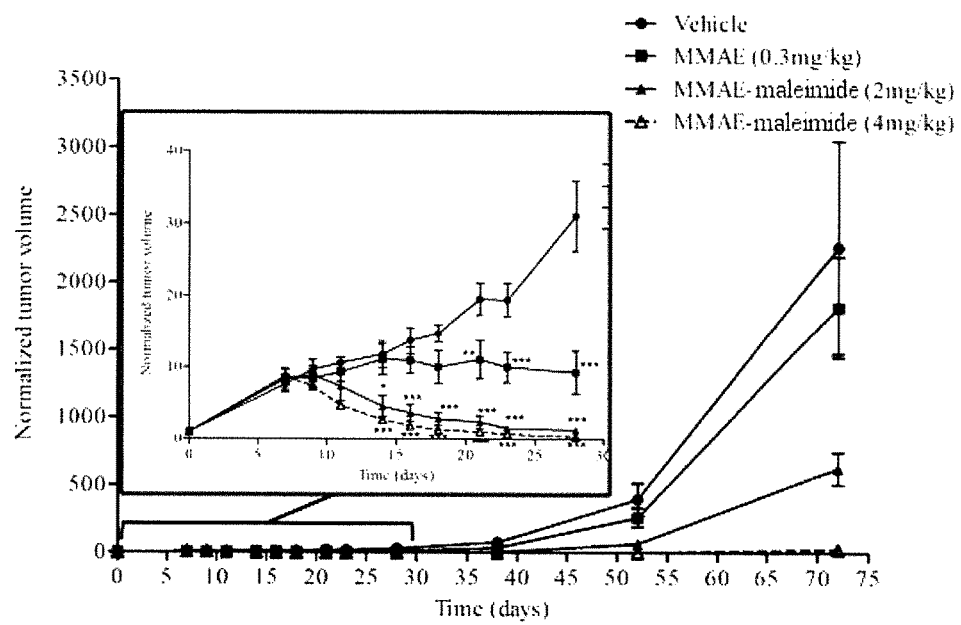
FIG. 2 illustrates the evolution of the volume of a human tumor of the pancreas of Mia Paca type grafted orthotopically in the mouse. Two injections of non-functionalized MMAE (0.3 mg/kg) or of a conjugate of formula (III), i.e. a bi-functionalized MMAE (2 or 4 mg/kg) are given on $D_7$ and $D_{14}$ after grafting. The tumor volume is evaluated by echography for 70 days after grafting. An insert represents this evolution on a time scale of 30 days post-grafting.

FIG. 2 illustrates the evolution of the tumor volume during a period of 70 days. A significant increase in the tumor volume is observed starting from day 35 for the control and the non-functionalized MMAE. Thus, non-functionalized MMAE is not suitable for the treatment of a pancreatic tumor. When the mice receive 2 injections ($D_7$ and $D_{14}$) of 2 mg/kg of bi-functionalized MMAE, i.e. a conjugate of formula (III), the progression of the tumor volume is slower than with the control or the non-functionalized MMAE. On the other hand, the administration of 2 injections ($D_7$ and $D_{14}$) of a dose of 4 mg/kg results in a total absence of tumor growth.

Example 3

Evaluation of the Therapeutic Efficacy of the Conjugate of Formula (III) In Vivo on a Murine Model of Human Pancreatic Cancer 1) Materials and Methods a) Animals Used The therapeutic efficacy of the conjugate of formula (III), as synthesized according to the reaction protocol described in example 1, was evaluated on 6-week-old female Balb/c Nude mice (Charles River France Laboratories— L'Arbresle) as indicated previously in example 2.

b) Orthotopically Grafted Human Pancreatic Tumor of Mia Paca Type

The orthotopically grafted human pancreatic tumor of Mia Paca type is such as that described in example 2.

c) Treatment Modes

The mice (5 animals per group) received a treatment when the tumor volumes reached a size of between 2.5 and 3.5 $cm^3$, i.e. volumes representative of the situation in humans where pancreatic cancers are detected late in most cases. The intravenous injections of the bi-functionalized MMAE conjugate, i.e. the conjugate of formula (III) (synthesized according to the reaction protocol described in example 1), were carried out once a week for 9 weeks at a dose of 4 mg/kg. The control group was treated with the excipient consisting of a mixture of DMSO and PBS (5%/95%). The evolution of the tumor volume was monitored by echography, as described in example 2.

2) Results

Figure 3:
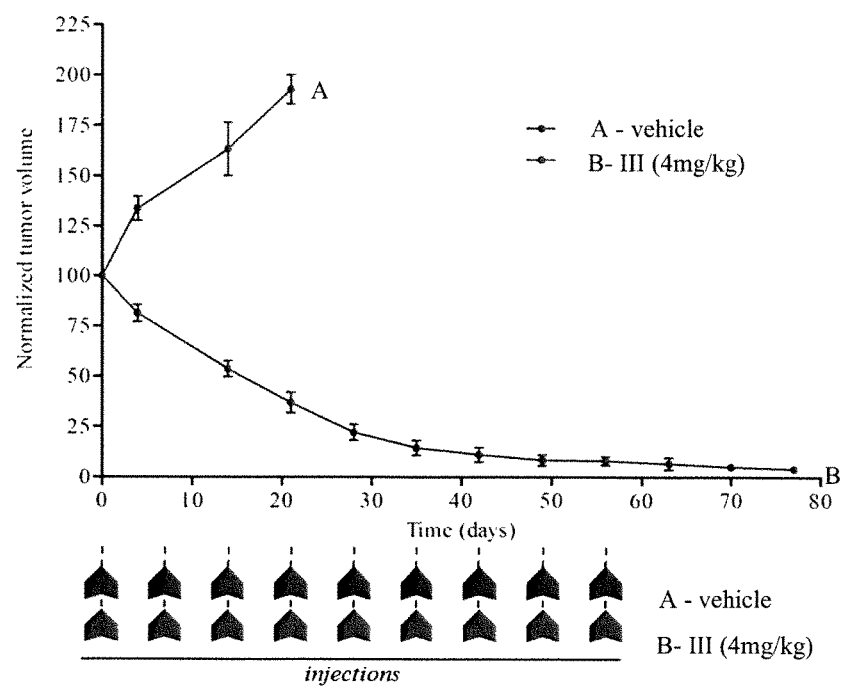
FIG. 3 illustrates the evolution of the volume of a tumor of the pancreas of MIA-PaCa type grafted orthotopically, followed by echography (5 animals per group). The conjugate of formula (III), at a dose of 4 mg/kg (A), and the excipient (B), were administered intravenously once a week for 9 weeks.

FIG. 3 illustrates the evolution of the volume of an orthotopically grafted pancreatic tumor of MIA-PaCa type, monitored by echography for 80 days.

A regression of the tumor volume ranging from 92% to 100% may be observed in the mice treated with the conjugate of formula (III) (panel A), whereas the animals not treated with the conjugate of formula (III) (vehicle, corresponding to the DMSO/PBS excipient; panel B) all succumbed within twenty days following the start of the therapeutic protocol.

Example 4

Evaluation of the Therapeutic Efficacy of the Conjugate of Formula (III) In Vivo on a Murine Model of Human Breast Cancer 1) Materials and Methods a) Animals Used The therapeutic efficacy of the conjugate of formula (III), as synthesized according to the reaction protocol described in example 1, was evaluated on 6-week-old female Balb/c Nude mice (Charles River France Laboratories—L'Arbresle) as indicated in example 3.

b) Orthotopically Grafted Human Breast Tumor of MDA-MB-231 Type

The MDA-MB-231 cells originate from a mammary adenocarcinoma from a 51-year-old woman. The MDA-MB-231 mammary cancer cell line was supplied by Caliper LifeSciences (Roissy, France). These cells were chosen because they make it possible to generate tumors of hypoxic nature, reflecting the clinical pathological situation.

These cells are modified to express the luciferase gene. The cells were cultured in 75 cm$^3$ flasks and maintained in a humidified incubator at 37° C. under an atmosphere consisting of air, with Eagle's Minimal Essential Medium (EMEM) supplemented with 10% of fetal calf serum, 1% of L-glutamine, 1% of sodium pyruvate, 1% of non-essential amino acids, 2% of sodium bicarbonate and 1% of penicillin and streptomycin.

For the implantations, the abdomens of the mice were disinfected with an iodinated povidone solution (Betadine®, ASTA Medica, Belgium). The needle was inserted into the subcutaneous space, at the level of the lower left teat. $2\times10^6$ MDA-MB-231-Luc cells in 100 µl of PBS was slowly injected using a 27-caliber needle. The needle was then slowly withdrawn. For this, the mice will be anesthetized by inhalation of isoflurane (2% in air).

c) Treatment Modes

The mice (6 animals per group) received a treatment 15 days after the tumor implantations. The intravenous injections were carried out once a week for 5 weeks with doses of 4 mg/kg of conjugate of formula (III) ($D_{15}$, $D_{22}$, $D_{29}$, $D_{36}$ and $D_{43}$). The control groups were treated either with MMAE alone with a dose of 0.3 mg/kg, or with the excipient consisting of a mixture of DMSO and PBS (5%/95%).

The evolution of the tumor volume was monitored by 3D echography. The measurements were carried out as described in example 2, on days 7, 11, 15, 19, 22, 25, 27, 29, 32, 34, 36, 39, 43 and 50.

2) Results

Figure 4:
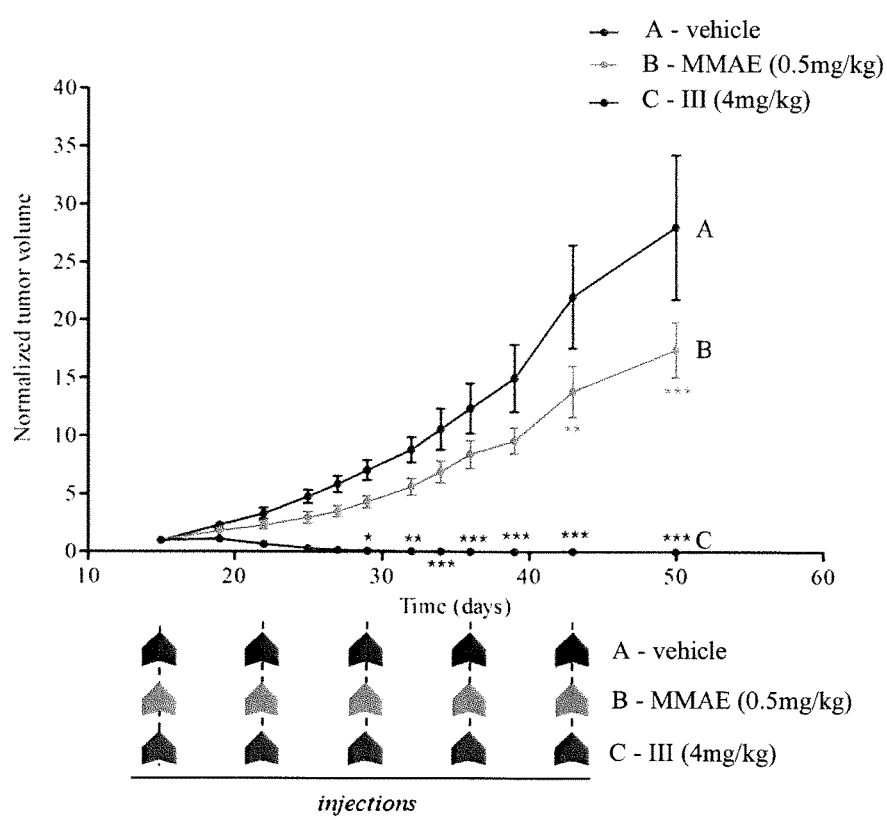
FIG. 4 illustrates the evolution of the volume of a human breast tumor of MDA-MB-231 type grafted orthotopically, followed by echography (6 animals per group). The animals treated with MMAE (B) received a dose of 0.5 mg/kg (intravenous) once a week for 5 weeks. The animals treated with the bi-functionalized MMAE conjugate (conjugate of formula (III) (C)) received a dose of 4 mg/kg (intravenous) once a week for 5 weeks. The control animals are treated with the excipient (vehicle (A)).

FIG. 4 illustrates the evolution of the volume of an orthotopically grafted human breast tumor of MDA-MB-231 type, monitored by echography for 50 days.

A total and long-lasting regression of the tumor can be observed in the animals treated with the conjugate of formula (III) (4 mg/kg) (panel C), whereas the free MMAE (panel B) produces only a very modest antitumor activity by comparison with the control animals (panel A). These results were obtained without visible side effects in the group of mice having received the conjugate of formula (III).

REFERENCES

Documents of Patent Type

U.S. Pat. No. 7,829,531
WO 2011/145068

Documents of Non-Patent Type

Kolb et al. Click Chemistry: Diverse Chemical Function from a Few Good Reactions. Angew. Chem. Int. Ed. 2001, vol. 40(11), 2004-2021.

Kratz et al. Probing the cysteine-34 position of endogenous serum albumin with thiol-binding doxorubicin derivatives. Improved efficacy of an acid-sensitive doxorubicin derivative with specific albumin-binding properties compared to that of the parent compound. J. Med. Chem. 2002, vol. 45, 5523-5533.

Legigan et al. The first generation of β-galactosidase-responsive prodrugs designed for the selective treatment of solid tumors in prodrug monotherapy. Angew. Chem. Int. Ed. 2012, vol. 51, 11606-11610.

Legigan et al. Synthesis and antitumor efficacy of a β-glucuronidase-responsive albumin-binding prodrug of doxorubicin. J. Med. Chem. 2012, vol. 55, 4516-4520.

Legigan et al. Synthesis and biological evaluations of monomethylauristatin E glucuronide prodrug for selective cancer chemotherapy. Eur. J. Med. Chem. 2013, vol. 67, 75-80.

Teming et al. Evaluation of RGD-targeted albumin carriers for specific delivery of auristatin E to tumor blood vessels. Bioconjugate Chem. 2006, vol. 17, 1385-1394.

Tranoy-Opalinski et al. β-glucuronidase-responsive prodrugs for selective cancer chemotherapy: an update. Eur. J. Med. Chem., 2014, vol 74, 302-313.

The invention claimed is:
1. A conjugate of general formula (I):

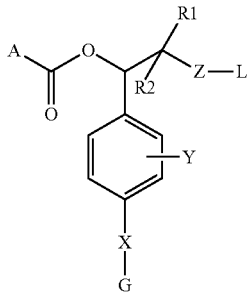

in which:
  A represents a radical of the dolastatin family or a derivative thereof,
  L represents a radical capable of reacting with an amino, hydroxyl or thiol function,
  G comprises a glucuronyl radical or a derivative thereof,
  Y represents H, or an electron-withdrawing radical chosen from $NO_2$, $CF_3$ and a halogen,
  $R^1$ and $R^2$ represent, independently of one another, H or a linear or branched, saturated or unsaturated $C_1$ to $C_{10}$ alkyl radical,
  Z represents a hydrocarbon-based spacer radical comprising, at each of its ends, covalent bond functions,
  X represents —O— or —$NR^3COO$—, with $R^3$ representing a hydrogen atom or a linear or branched, saturated or unsaturated $C_1$ to $C_{10}$ alkyl radical, the bond with the G radical being provided by the oxygen atom (—O—),
an isomer thereof and/or a pharmaceutically acceptable salt thereof.

2. The conjugate according to claim 1, in which Y represents $NO_2$ in the ortho position of X, and $R^1$ and $R^2$ represent H.

3. The conjugate according to claim 1, in which A represents a radical which derives from dolastatin 10, from auristatin PE, from auristatin E, from monomethyl auristatin E and derivatives thereof.

4. The conjugate according to one of claim 1, in which L comprises a unit capable of reacting with a free amino, hydroxyl or thiol function carried by a macromolecules having a free thiol function.

5. The conjugate according to claim 1, in which L represents a unit of maleimidocaproyl.

6. The conjugate according to claim 1, in which Z represents a $Z^1$—$Z^2$—$(Z^3)_m$ radical, in which:
  m represents 0 or 1,
  $Z^1$ represents an L-click linker function between the carbon carrying the $R^1$ and $R^2$ functions, and the $Z^2$ function,
  $Z^2$ represents a linear or branched, saturated or unsaturated $C_1$-$C_{10}$ alkylene group optionally interrupted with one or more heteroatoms chosen from O or N, a glycosyl radical, an O—$(CHR^4$—$CHR^5$—O—$)_p$ or N—$(CHR^4$—$CHR^5$—O—$)_p$ radical in which p represents a natural integer ranging from 1 to 20, and $R^4$ and $R^5$ represent, independently of one another, H or $CH_3$, with the proviso that $R^4$ and $R^5$ do not simultaneously represent $CH_3$, a group derived from an amino acid or from a peptide, or a combination of these groups, one end of $Z^2$ producing a covalent bond with L, either directly via an ether function, or indirectly via a $Z^3$ function,
  $Z^3$ represents a function of ester, amide, ether, carbamate or carbonate established between the $Z^2$ function and the L radical.

7. The conjugate according to claim 1, of formula (III) below:

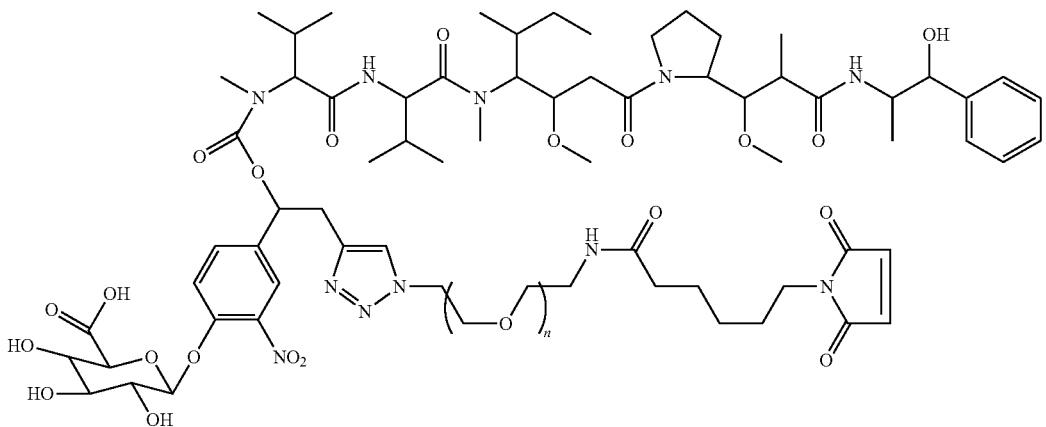

an isomer thereof and/or a pharmaceutically acceptable salt thereof.

8. A prodrug comprising at least one molecule of the conjugate according to claim 1, said molecule of the conjugate being linked via a covalent bond to an albumin molecule or a fragment or derivative thereof.

9. The prodrug according to claim 8, in which the covalent bond is established with the thiol function of the cysteine in position 34 of the albumin.

10. The prodrug according to claim 8, the formula of which is formula (VII) below:

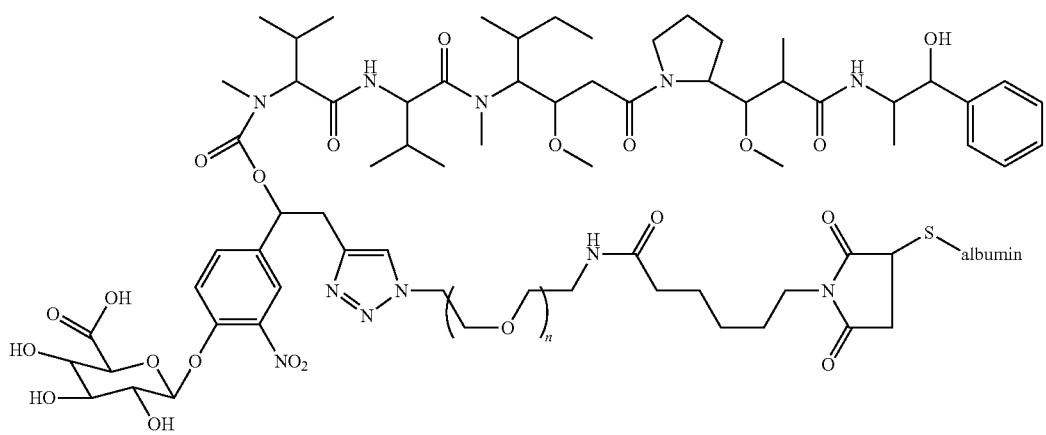

(VII)

an isomer thereof and/or a pharmaceutically acceptable salt thereof.

11. A pharmaceutical composition comprising at least an effective amount of at least one conjugate as defined according to claim 1.

12. The conjugate according to claim 1 in which A represents a radical which derives from monomethyl auristatin E and derivatives thereof.

13. The conjugate according to claim 1, in which L comprises a free thiol function.

14. A pharmaceutical composition comprising at least an effective amount of at least one prodrug as defined according to claim 10.

15. A method for treating breast or prostate cancer, comprising the administration of a conjugate of general formula (I) according to claim 1.

16. A method for treating breast or prostate cancer, comprising the administration of a conjugate of general formula (I) according to claim 10.

17. A method for treating breast or prostate cancer, comprising the administration of a conjugate of general formula (I) according to claim 12.

* * * * *